US005597575A

United States Patent [19]
Breitbarth

[11] Patent Number: 5,597,575
[45] Date of Patent: Jan. 28, 1997

[54] COMPOSITION FOR STIMULATING AND INDUCING HAIR GROWTH

[76] Inventor: Richard Breitbarth, 10 Old Bloomfield Ave. PO Box 682, Pinebrook, N.J. 07058

[21] Appl. No.: 254,568

[22] Filed: Jun. 6, 1994

[51] Int. Cl.$^6$ .............................. A61K 7/06; A61K 9/10; A61K 9/14; A61K 9/18

[52] U.S. Cl. ..................... 424/401; 424/450; 424/490; 424/489; 514/770; 514/880; 514/937; 514/952; 514/975; 514/167

[58] Field of Search ..................... 424/70.1, 489, 424/490, 450, 401; 514/880, 167

[56] References Cited

U.S. PATENT DOCUMENTS

| | | | |
|---|---|---|---|
| 4,897,269 | 1/1990 | Mezei | 424/450 |
| 5,183,817 | 2/1993 | Bazzano | 514/256 |
| 5,427,776 | 6/1995 | Isnard | 424/70.1 |
| 5,486,509 | 1/1996 | Jimenez et al. | 514/167 |

*Primary Examiner*—James M. Spear
*Attorney, Agent, or Firm*—Evelyn M. Sommer

[57] ABSTRACT

This application proposes a new topical treatment for the stimulation and induction of hair growth as well as for preventing further hair loss. These pharmacologic results would be achieved by stimulation of an inactive hair follicle or by reversing the dysfunction of the hair follicles or by improvement of the general physiologic state of the scalp skin. It would also stimulate the maturation and differentiation of those cells specifically involved in hair growth either directly or by stimulating the organelles and supporting structures associated with the hair follicle. The topical composition comprises vitamin $D_3$ or various nitro-benzoic acids esters thereof, or the biologically active metabolites of vitamin $D_3$ preferabiy affixed, during preparation to microparticulate charged non-metaliic microparticles and aloe. The final concentration of vitamin $D_3$ in the composition is 0.5% or 500,000 IU by volume. To this composition other agents, vitamins, aminoacids, trace elements or minerals, or polysaccharides can be added in nontoxic amounts. In a trial of a series of patients treated with the composition all were noted to nave cessation of hair loss followed by hair regrowth.

16 Claims, No Drawings

COMPOSITION FOR STIMULATING AND INDUCING HAIR GROWTH

This application relates to a new topical composition and treatment method for the stimulation and induction of hair growth as well as for the prevention of further hair loss. More particularly this invention is directed to compositions for stimulating and inducing hair growth and for preventing hair loss, comprising vitamin $D_3$, a nitrobenzoic acid ester thereof or a biologically active metabolite of vitamin $D_3$ as active ingredient, and to methods of preparing and using such compositions. Hair loss in individuals amenable to treatment with the compositions of the invention, is of the androgenic alopecia type and expressed in males as baldness of the vertex of the scalp and in females as diffuse hair loss or thinning of the frontal and parietal areas. Hair growth in accordance with the invention is achieved by stimulation of the hair follicles as well as induction of maturation and differentiation of those epidermal cells involved in hair growth.

The compositions of the invention are applied topically as hereinafter set out and are comprised of vitamin $D_3$, nitrobenzoic acid ester thereof, for example p-nitrobenzoate or 3,5-dinitrobenzoate or a biologically active metabolite of vitamin $D_3$ such as 25 $(OH)_2$-24-oxo-$D_3$, 23,25 $(OH)_3$-24-oxo-$D_3$, or 24R,25$(OH)_3$-$D_3$. Preferably the vitamin $D_3$ is affixed to a non-metallic microparticulate carrier. Still more preferably aloe is present. Additionally any/or combinations of any of the following substances; vitamin A, vitamin C, vitamin $B_6$, vitamin E, panthenol, amino acids, hyaluronic acid or its sodium salt, minerals, trace elements, fragrance, color are present as is a pharmaceutically acceptable vehicle.

To date, the FDA has banned all nonprescription baldness prevention or reversal drugs for the reason that careful study has failed to find any preparation that scientifically can be shown to safely and effectively prevent hair loss or grow new hair (OTC Drug Review 1993). At present, there are no conditionally approved active ingredients for use in the treatment of male pattern baldness or diffuse baldness in women.

Previously proposed and tested compounds for use in treating the aforesaid conditions include ascorbic acid, benzoic acid, estradiol, lanolin, tetracyclines, wheat germ oil, etc. However, only one drug has been authorized for use in the treatment of hair loss but a prescription is required for its use. That drug is minoxidil (Rogaine(tm), Upjohn). This drug has been found safe and effective for stimulation of hair growth. The drug, however, has limited effectiveness, and is successful only in a minority of men (39%) and 50% of women. In most instances, where treatment is successful, these individuals have shown only a moderate amount of hair growth. Minoxidil is only recommended for use in healthy individuals without any skin (scalp) abrasions. No effect is seen for months and treatment is expensive. Patients have to be seen by their physician periodically to assure that no side effects from the treatment nave occurred. Results with placebo treatment approximate those that are seen in minoxidil treated patients.

The active agent proposed for use in the instant compositions is vitamin $D_3$ or one of the various benzoic acid esters thereof, for example p-nitrobenzoate ($C_{34}H_{47}NO_4$), 3,5-dinitrobenzoate ($C_{34}H_{46}N_2O_6$) or vitamin $D_3$'s biologically active metabolites such as 25$(OH)_2$-24-oxo-$D_3$, 23,25$(OH)_3$-24-oxo-$D_3$, or 24R,25$(OH)_3$-$D_3$. This vitamin $D_3$ component in a pharmaceutically acceptable carrier when applied topically has been found to successfully stimulate hair growth.

Preferably the vitamin $D_3$ component is affixed to a non-metallic microparticulate particle. The success of utilizing such a soiid particle, depends largely on mimicking the interaction that would occur if the component affixed were in free solution. The qualities cf the ideal particles (matrix materiais) are dependent on their very small size, uniformity, spherical shape and rigid nature and their good flow properties. The particles should not interact with proteins in general so that there is no non-specific adsorption. The particles should possess a supply of chemical groups which can be activated to allow the covalent attachment of a variety of agents and they should be chemically stable to the conditions of coupling, adsorption and elution. Until recently, almost all matrix materials have been derivatives of cellulose, polystyrene or synthetic poly-amino acids, cross-linked dextrans, polyacrylamide gels and agarose. Although there is a diversity of insoluble non-metallic carriers, certain restrictions limit their usefulness to specific situations, e.g., cellulose's usefulness is limited by its fibrous and non-uniform character which impedes proper penetration of large molecules. Polystyrene, polyacrylamide and cross linked dextran gels have low porosity. The beaded derivatives of agarose are ideal for use in many situations. The beads are uniform, small, stable, and spherical and have a high capacity for substitution but their usefulness is however limited by temperature lability and by their tendency to break down.

The carriers preferred for use herein for affixing the vitamin $D_3$ include silica, charcoal, alumina and liposome microparticles.

Silicas which are preferred microparticles are among the most widely used materials. The silica materials are available commercially as porous granules of high quality silica glass permeated by inter-connecting pores of uniform and precisely controlled size. They are insoluble and unaffected by changes in their immediate environment, e.g., pH or ionic strength. They are resistant to microbial attack and can be sterilized by disinfectants or heat. Like all silica glasses the surface of porous glass beads consists of hydroxyl groups which exhibit a slight negative surface charge in aqueous solution.

Silica particles are available in at least two types, macroparticulate and microparticulate. The macroparticular silica particles have a mean particle diameter of >40 μm and are completely porous. The microparticular sliica particles as used herein are particles having a mean particle diameter of between 3 and 10 μm and are completely porous. They have either a spherical or moderately irregular shape. Microparticulate silica particles display the highest efficiencies as well as the greatest loading capacity. The silica particles can be used directly or modified by coating or chemically bonding an active phase onto the silica surface.

Alumina (aluminum oxide) $Al_2O_3$ particles are also suitable for use herein. Alumina occurs in nature and is a white crystalline very hard powder, insoluble in water. When activated it can be used for attachment of other molecules. Alumina microparticles have an average particle size of about 7 μm.

Similarly to alumina, charcoal (Darco) a water insoluble non-metallic microparticulate material, can be used for attachment of other molecules in this case the vitamin $D_3$ component.

Liposomes can also be used effectiveiy and are spherical particles distributed in an aqueous medium and are formed of a lipid-bilayer enclosing an aqueous compartment. Liposomes are prepared by sonicating a lipid in an aqueous medium. The liposome "membrane" lipid-bilayer allows for movement of active agents i.e., the vitamin $D_3$ component in and out of the sphere.

The choice of microparticulate material is dependent on the specific conditions that may be unique for each application. However silica microparticles are preferred.

The vitamin $D_3$, its nltrobenzoic acid ester or a biologically active metabolite of vitamin $D_3$, will be attached to the microparticles during the admixing for formulating the composition(s). In this admixing the active agent is affixed to the non-metallic microparticulate carrier directly or on to a modified or coated particle in such a manner that the vitamin $D_3$ can readily and controllably be released and then absorbed through the skin.

Hair follicles are appendages of the skin and are present on almost all areas of skin with few exceptions (palm, sole, and eyelid). Associated with the hair follicles are specific glands (sebaceous, produce sebum), muscles, blood vessels and other structures. The hair and its associated parts are contained in the follicle. The distal end of the follicle is in the dermis and the upper portion exits through the epidermis. This invention is concerned with the hair normally found on the scalp. The growth of such hair is cyclical. There are three stages: anagen the growing phase, catagen an involution phase and telogen a resting stage. The hair follicle Is lined with epithelium similar to that found on the skin and the ducts of the associated glands, as well as the sweat glands allow for markedly increased surface for absorption of drugs or other agents applied to the skin and in this application to the scalp.

Few drugs readily penetrate the intact skin. Absorption (percutaneous) of those that do is proportional to the surface area over which they are applied and to their lipid solubility. Irritation or inflammation, are conditions that increase cutaneous blood flow and enhance absorption. Absorption can also be enhanced by hydration as well as by rubbing the preparation into the skin. Topical application for administering drugs and even for controlled release of drugs is now used extensively. This route i.e., penetration through the skin prevents the extensive first pass metabolism seen after oral administration.

The D vitamins are a group of compounds, all of which are sterols and occur in nature. Certain of these sterols (known as pro-vitamins D) when subjected to long wave ultra violet light (about 265 mu) acquire the physiologic properties of curing or preventing rickets. The two most important vitamins D for nutritional purposes are $D_2$ (activated ergosterol, also known as calciferol or viosterol) and $D_3$ (activated 7-dehydrocholesterol) the form which occurs in nature in the fish liver oils. Vitamin $D_2$ is found in the plant kingdom (yeast, fungi etc.) Man and other mammals can synthesize vitamin $D_3$ in the body. Neither vitamin $D_2$ nor vitamin $D_3$ is active as such. Before becoming physiologically active, each must undergo two hydroxylations both of which require specific enzymes. These reactions occur in the liver and kidney. The biological action of these metabolites of vitamin $D_3$ (1,25-$(OH)_2$D is the most potent) are: 1) Stimulation of calcium absorption by the small intestine 2) Stimulation of calcium resorption from bone acting with parathyroid hormone, 3) Increase the calcium reabsorption in the kidney, 4) Stimulation of intestinal absorption of phosphate independent of intestinal calcium absorption and 5) probably of most importance to this application is the action of vitamin $D_3$ on differentiation of a variety of cells e.g,. progenitor cells into osteoclasts. In skin (epidermis), there is a series of epithelial cell differentiation steps leading to maturation of these epidermal cells to contain mature keratin (the protein of hair).

The deterioration of vitamin $D_3$ is negligible even after storage for one year, however in the form of the various nitro-benzoic esters, the vitamin $D_3$ can be stored indefinitely without undergoing deterioration.

Among the findings associated with application of vitamin $D_3$ is irritation. This pharmacologic action is of significance in stimulating hair growth and is a technique sometimes used by dermatologists to stimulate hair growth.

Calcitriol (Abbott) is the most active form of vitamin $D_3$. Calcijex (Abbott) is synthetically manufactured calcitriol and is available as a sterile, isotonic, clear, aqueous solution suitable for intravenous injection (each ml contains 1 or 2 mcg). Calcitriol is a colorless crystalline compound. It is soluble in organic solvents but relatively insoluble in water.

Calcitriol (Roche Rocaltrol) comes in capsule form (0.25 or 0.5 mcg). This synthetic vitamin D analog (calcitrol) is a colorless, crystalline compound. It has a MW of 416.65 and is soluble in organic solvents but relatively insoluble in water.

Calciferol (tm)(Schwarz Pharma), in oil is available as 500,000 IU/ml.

The composition of the invention is to be comprised of 0.25 to 1% vitamin $D_3$, 1.000,000 IU activity level in corn oil or other suitable oll carrier. Preferably the composition additionally contains 2.5 to 15% of microparticulate material having a suitable surface charge, i.e., silica particles. More preferably there is present 0.5% Sutacide A, 1.5 to 3% aloe, (10:1 concentration), and 3.5 to 6% of a surfactant. The balance is distilled water. The preferable composition exists as a microdispersion.

Aloe (*Aloe vera*) is a genus with 200 species comprised mainly of South African succulents. It has been used in healing since ancient times. The inspissated juice of several varieties of the *Aloe vera* plant are used in the treatment of burns. Its properties are said to be due to the presence of aloin a bitter principle and toxic astringent, but primarily it is used pharmacologically as a moisturizer and soothing agent.

Other substances which may be admixed in varying combinations to the basic composition include:

1. Vitamin A, its congeners or derivatives—vitamin A and its derivatives are key substances in modulation of epithelial tissues. They have been shown to affect normal or abnormal epidermis, hair and other epithelial structures. In physiologic amounts, the vitamin A famiiy (retinol, retinoic acid etc.) is believed to be essential for maintenance of normal epithelial differentiation.

2. Vitamin C—vitamin C deficiency is associated with scurvy, the earliest manifestation of this disorder occurs in the skin. Associated with this disorder is excessive hair loss.

3. Vitamin $B_6$—among the many manifestatmons of vitamin deficiency are cutaneous abnormalities.

4. Panthenol (Pantothenlc acid) is a component of coenzyme A. A deficiency of this vitamin is associated with a dermatitis.

5. Vitamin E—the biological activity of this vitamin (a tocopherol) has been attributed to its action as an antioxidant. The tocopherols can protect various compounds against oxidation and subsequent loss of activity.

6. Hyaluronic acid or its sodium salt—This polysaccharide is associated with the ground substance of skin (dermis). It is a viscous jelly-like substance and serves to support the fibers associated with skin (elastic, collagen etc,) as well as to maintain the softness associated with youthful skin. The hair follicle is embedded in the dermis.

7. Amino acid—Any amino acid, singly or in combination can be used, e.g., the sulfur containing amino acids make up a large part of the keratin (hair) molecule. These amino acids are major constituents of the proteins of the epidermis. An example of an amino acid suitable for use herein is tryptophan, a precursor of niacin.

8. Minerals and trace metals—Iron—epithelial changes have been observed in iron deficiency. This includes altered hair growth. Iron deficiency is associated with diffuse hair loss, with a favorable response to iron replacement. Zinc—adequate levels are recognized as being of importance to the maintenance of normal skin and hair. Zinc plays a major role in wound healing and a deficiency of this element is associated with skin and hair pathology.

The foregoing additives, singly or in varied combinations can be added to the compositions of the invention. These additives are to be utilized in the conventional amounts. The vitamin $D_3$, the active agent herein in its active form (synthetic) when used in the preferred embodiments of the invention will be attached to the charged ionic groups of the non-metallic microparticulate carrier, directly or on to the modified or coated particles in such a manner that the vitamin $D_3$ can readily and controllably be released from the particles by small pH or salt changes (sweat etc.), or by the addition of an eluting solution, and be available for absorption into the hair follicle and surrounding skin of the scalp. When formulated the compositions containing the non-metallic microparticulate particles and the vitamin $D_3$ will be in the form of a solution in a vehicle preferably containing aloe.

The active vitamin $D_3$ is known to be involved in calcium and phosphate metabolism but when applied topically it may have in addition a vasodilating effect. Arterial dilating drugs have been shown to stimulate hair growth (minoxidil). The non-metallic microparticle drug combination may also be an irritant leading to additional vasodilation and increased drug absorption. Calcium seems to have no role in keratinization but calcium metabolism is very important in the biochemistry of the dermal layer of the skin (collagen and ground substance) and indirectly may play a role in the physiology of the hair follicle. Most importantly is the role of the vitamin $D_3$ metabolites in differentiation and maturation of cells and their role in the hair follicle.

The compositions of the invention for use in the topical treatment of androgenic alopecia can contain the following agents in amounts of about:

1. Vitamin $D_3$ (1,000,000 IU activity level (Roche) in corn oil or other suitable oil carrier—0.25%–1.0% but preferably 0.5% by volume. (The vitamin $D_3$ in the form of its nitro-benzoic acid ester or a biologically active metabolite can be substituted for the vitamin $D_3$).

2. Non-metallic microparticulate particles—7.5%–15% but preferably 15% by volume.

3. Tween 20 or 80 a surfactant—3.5%–6.0% but preferably 5.0% by volume.

4. Sutacide A, a preservative—ethyl or methylparaben could be used, but sutacide A is preferred in a final concentration of 0.3%.

5. Aloe—(pH adjusted previous to use) 1.5%–3% but preferably 2.5%.

6. The remainder is water as required to bring the total percentage to 100%.

7. Fragrance or color could be added if desired.

The foregoing materials are preferably present singly or in combination in addition to the active component, vitamin $D_3$, alone or in combination with the microparticles.

Additionally any of the listed vitamins, amino acids, trace metals or minerals or polysaccharides could be added during the manufacture of this basic composition or after, utilizing the basic composition as vehicle.

The method for producing the basic composition comprises the following procedure:

The contents for the composition are continually stirred in a mixing vessel with a homogenizer (a high shear mixer (Greerco). The constituent reagents are added to the water, under constant stirring in the mixing vessel. The first agent introduced is the preservative Sutacide A, in an amount between 0.3 and 0.5%, preferably 0.3% by volume. (Sutacide A is a preservative which is extracted from grapefruit seeds). The microparticulate (preferably ionically charged silica particles) are added next in an amount of 7.5 to 15%, preferably 15% by volume. Vitamin $D_3$ in corn oil is first premixed with Tween 20 so that a final concentration of 3.5 to 6% but preferably 5% Tween 20 in the admixture will contain 0.25 to 1% but preferably 0.5% vitamin $D_3$, that is, 0.5 ml of vitamin $D_3$, (1,000,000 IU/ml) in corn oil is present in 5 ml Tween 20. This mixture is introduced into the mixing vessel (5 ml/100 ml). Finally aloe, which had been buffered with sodium hydroxide to pH 7–10 is added to give a final concentration of 1.5 to 3% but preferably 2.5%. The pH of the resultant solution is adjusted with citric acid (USP) to 7 to 10. Water is added as required to bring the total percentage to 100%.

Accordingly, compositions useful in the practice of this invention can also include pharmacologic amounts of other vitamins, amino acids, metals or trace elements added to the basic composition consisting of vitamin $D_3$ and a suitable liquid carrier and aloe. Most preferably silica microparticles are present. Still more preferably the basic composition includes in addition to the vitamin $D_3$, the microparticles and aloe in the form of a microdispersion thereof in a suitable liquid i.e., aqueous or oily carrier.

The aforementioned additives may for example be present as follows:

| Agent | US RDA (adults) |
|---|---|
| Vitamin A | 5,000 IU |
| Vitamin $B_1$ | 1.5 mg |
| Vitamin $B_6$ | 2.0 mg |
| Vitamin C | 60 mg |
| Vitamin E | 30 IU |
| Biotin | 0.15 mg |
| Pantothenic Acid | 10 mg |
| Iron | 18 mg |
| Zinc | 15 mg |
| Tryptophan | |
| Cysteine | |
| Cystine | |
| Methionine | |
| Hyaluronic Acid | |

Any one or any multiple of the following amino acids, vitamins or metals could be admixed with the composition during preparation or added subsequently. The table above lists the daily requirements of each substance shown, (where known). All of the above substances are known to be involved in maintaining a healthy epidermis as well as maintaining the appendages associated with the epidermis. This amount, or preferably greater amounts, would be added to the basic composition. In most instances the above reagents are not known to be toxic, particularly when applied topically. The final composition would be applied to the scalp in a volume of about 2.5–5 ml.

An effective vitamin $D_3$ containing composition in accordance with this invention would have the formulation of the basic composition to which would be added pantothenic acid (100 mg, 0.1%), iron (200 mg, 0.2%), and Zinc (250 mg, 0.25%), in 100 ml of basic composition.

Another effective composition in accordance with this invention would have the formulation of the basic composition to which would be added vitamin E (50 IU) and Zinc (250 mg, 0.25%).

In similar manner, depending on solubility and compatibility of the added agents, they could be added directly in water or oil with and without the addition of further surfactant, at the time of preparation.

The composition(s) are to be applied drop wise to the scalp and massaged in with the finger tips over a period of at least 5 minutes once a day.

A preferred composition exemplifying the invention is the following:

| Agent | Per Cent |
| --- | --- |
| vitamin $D_3$ | 0.5 |
| Sutacide A | 0.3 |
| aloe | 2.5 |
| silica microparticles | 15.0 |
| Tween 20 | 5.0 |

Another composition for exemplifying the invention is the following:

| Agent | Per Cent |
| --- | --- |
| vitamin $D_3$ | 0.5 |
| Sutacide A | 0.3 |
| aloe | 2.5 |
| alumina microparticles | 10.0 |
| Tween 20 | 5.0 |
| vitamin E | 50 IU |
| zinc | 0.25 |

Clinical data: The preferred composition has been evaluated in trials with 5 healthy males aged 24–46 years and one healthy female, 20 years old. After 2 to 4 weeks of daily treatment there was cessation of hair loss followed by regrowth. After 2 months the results in all patients were good with appreciable hair regrowth.

I claim:

1. A composition for stimulating and inducing hair growth which comprises a member selected from the group consisting of vitamin $D_3$, the nitro-benzoic acid esters of vitamin $D_3$, and the biologically active metabolites of vitamin $D_3$ affixed to microparticulate non-metallic particles having a particle size of between 3 and 10 μm in the form of a microdispersion thereof in a pharmaceutically acceptable vehicle wherein said microparticulate particles exhibit a negative charge about that of an aqueous solution of silicas due to the presence of charged ionic groups.

2. A composition according to claim 1 wherein said vitamin $D_3$ is attached to said microparticulates via said charged ionic groups.

3. A composition for stimulating and inducing hair growth which comprises a member selected from the group consisting of vitamin $D_3$, the nitro-benzoic acid esters of vitamin $D_3$, and the biologically active metabolites of vitamin $D_3$ affixed to microparticulate non-metallic particles in the form of a microdispersion thereof in a pharmaceutically acceptable vehicle wherein said microparticulate particles are selected from the group consisting of silica, alumina, and charcoal.

4. A composition according to claim 3 comprising the following:

| | |
| --- | --- |
| Vitamin $D_3$ (1,000,000 IU activity level | 0.25–1.0% volume |
| Microparticulate non-metallic particles having a negative surface charge | 2.5–15.0% by volume |
| Surfactant | 3.5–6.0% by volume |
| Preservative | 0.3% by volume |
| Aloe (10:1 concentration) | 1.5–3.0% by volume |
| Water | balance |

5. A composition according to claim 3 comprising the following:

| | |
| --- | --- |
| Vitamin $D_3$ (1,000,000 IU activity level | 0.5% by volume |
| Microparticulate silica particles having a negative surace charge | 15.0% by volume |
| Aloe (10:1 concentration) | 2.5% by volume |
| Sutacide A | 0.3% by volume |
| Surfactant | 5.0% by volume |
| Water | Balance |

6. A composition according to claim 5 additionally containing at least one member selected from the group consisting of vitamin A, vitamin B, vitamin $B_6$, vitamin C, vitamin E, amino acids, hyaluronic acid or its sodium salt, panthenol, trace minerals, fragrance and color.

7. A composition according to claim 5 wherein said microparticulates are selected from the group consisting of silica, charcoal, or liposomes.

8. Method of preparing composition according to claim 5 which comprises the steps of:

a) introducing into a mixing vessel, equipped with a high sheer mixer the preservative Sutacide A;

b) introducing into the mixing vessel the microparticulate particles;

c) thereafter introducing said vitamin $D_3$ in corn oil;

d) introducing into the resulting mixture said aloe which has previously been buffered to a pH of 7–10;

e) adjusting the pH of the resultant microdispersion with citric acid to a pH of 7–10; and f) adding water to achieve the desired final concentration.

9. Method according to claim 8 which comprises introducing the preservative in step a) and wherein in step c) said vitamin $D_3$ in corn oil is admixed with the surfactant Tween 20.

10. Method according to claim 8 which comprises introducing into said mixing vessel at least one member selected from the group consisting of vitamin A, vitamin B, vitamin $B_6$, vitamin C, vitamin E, trace minerals, amino acids, hyaluronic acid or its sodium salt, panthenol, fragrance and color.

11. Method according to claim 10 wherain said element is iron or zinc.

12. Method according to claim 10 wherein said amino acid is at least one member selected from the group consisting of tryptophan, cystine, and methionine.

13. Method of treating a subject for stimulating and inducing hair growth in such subject which comprises applying an effective amount of composition according to claim 1 to the scalp and massaging the drops of composition into the scalp for a period of five minutes once a day.

14. Method of treating a subject for stimulating and inducing hair growth in such subject which comprises applying an effective amount of a composition according to claim 1, in a drop wise fashion, to the scalp and massaging the drops of composition into the scalp for a period of five minutes once a day.

15. Method of treating a subject for stimulating and inducing hair growth in such subject which comprises applying an effective amount of a composition according to claim 1, in a drop wise fashion, to the scalp and massaging the drops of composition into the scalp for a period of five minutes a day.

16. Method for treating a subject for stimulating and inducing hair growth in such subject which comprises applying an effective amount of a composition containing as active ingredient a member selected from the group consisting of vitamin D3, the nitro-benzoic acid esters of vitamin D3 and the biologically active metabolites of vitamin D3, said member of said group being affixed to microparticulate non-metallic particles having a particle size of between 3 and 10 μm wherein said microparticulate particles exhibit a negative charge about that of an aqueous solution of silicas due to the presence of charged ionic groups and said microparticles being in the form of a microdispersion contained in a pharmaceutically acceptable vehicle.

* * * * *